United States Patent
Krauss et al.

(10) Patent No.: US 10,555,706 B2
(45) Date of Patent: Feb. 11, 2020

(54) METHOD FOR GENERATING IMAGES BY MEANS OF A COMPUTED TOMOGRAPHY DEVICE, AND COMPUTED TOMOGRAPHY DEVICE

(71) Applicant: Siemens Healthcare GmbH, Erlangen (DE)

(72) Inventors: Bernhard Krauss, Burgthann (DE); Bernhard Schmidt, Fuerth (DE); Karl Stierstorfer, Erlangen (DE); Eric Fournie, Erlangen (DE); Markus Juergens, Adelsdorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/351,722

(22) Filed: Mar. 13, 2019

(65) Prior Publication Data

US 2019/0290227 A1  Sep. 26, 2019

(30) Foreign Application Priority Data

Mar. 23, 2018  (DE) .................. 10 2018 204 517

(51) Int. Cl.
*G06K 9/00*  (2006.01)
*A61B 6/03*  (2006.01)
(Continued)

(52) U.S. Cl.
CPC ............ *A61B 6/032* (2013.01); *A61B 6/0407* (2013.01); *A61B 6/4007* (2013.01);
(Continued)

(58) Field of Classification Search
None
See application file for complete search history.

(56) References Cited

U.S. PATENT DOCUMENTS

| | | | |
|---|---|---|---|
| 2003/0195416 A1* | 10/2003 | Toth | A61B 6/032 600/427 |
| 2004/0102688 A1* | 5/2004 | Walker | A61B 6/032 600/407 |

(Continued)

FOREIGN PATENT DOCUMENTS

| | | |
|---|---|---|
| DE | 102009007236 A1 | 8/2010 |
| DE | 102011005554 A1 | 9/2012 |

(Continued)

OTHER PUBLICATIONS

German Patent Document for German Application No. 102018204517.8 dated Feb. 20, 2019 (English Translation).

(Continued)

*Primary Examiner* — Shervin K Nakhjavan
(74) *Attorney, Agent, or Firm* — Harness, Dickey & Pierce, P.L.C.

(57) ABSTRACT

To generate images, in which a first row area of a multiple-row detector is illuminated with a first X-ray spectrum and a second row area of the multiple-row detector, trailing in the direction of travel, is illuminated with a second X-ray spectrum, image data is recorded at a pitch chosen such that one slice image can be reconstructed in each case for a sectional position for the first and the second row area. Correspondingly, for the sectional position, the respective slice image for the first and the second row area is reconstructed. For a third row area, illuminated with the first and the second X-ray spectrum, a reference sectional image is reconstructed as a slice image. To generate motion-reduced first and second spectral images assigned to the first and second row area respectively, the slice images of the first and second row areas are registered to the reference sectional image.

20 Claims, 3 Drawing Sheets

(51) Int. Cl.
*A61B 6/04* (2006.01)
*A61B 6/00* (2006.01)
*G06T 11/00* (2006.01)
*G16H 30/40* (2018.01)
*A61B 6/02* (2006.01)

(52) U.S. Cl.
CPC ............ *A61B 6/4441* (2013.01); *A61B 6/027* (2013.01); *A61B 6/4447* (2013.01); *A61B 6/466* (2013.01); *A61B 6/482* (2013.01); *A61B 6/503* (2013.01); *A61B 6/5258* (2013.01); *G06T 11/005* (2013.01); *G06T 2211/412* (2013.01); *G16H 30/40* (2018.01)

(56) References Cited

U.S. PATENT DOCUMENTS

| | | | |
|---|---|---|---|
| 2007/0206880 A1* | 9/2007 | Chen | G06K 9/00 382/294 |
| 2009/0076369 A1* | 3/2009 | Mistretta | A61B 6/482 600/407 |
| 2010/0195888 A1 | 8/2010 | Bruder | |
| 2012/0039519 A1* | 2/2012 | Fei | A61B 6/12 382/131 |
| 2012/0238870 A1* | 9/2012 | Smith | A61B 6/025 600/431 |
| 2013/0114871 A1* | 5/2013 | Berkus | A61B 6/5205 382/131 |
| 2014/0086383 A1* | 3/2014 | Huwer | A61B 6/505 378/5 |
| 2016/0135775 A1* | 5/2016 | Mistretta | A61B 6/5247 600/411 |
| 2017/0055932 A1* | 3/2017 | Lee | A61B 6/5264 |

FOREIGN PATENT DOCUMENTS

DE 102011007529 A1 10/2012
DE 102011083647 A1 3/2013

OTHER PUBLICATIONS

German Decision to Grant and English translation thereof dated Jun. 14, 2019.

* cited by examiner

METHOD FOR GENERATING IMAGES BY MEANS OF A COMPUTED TOMOGRAPHY DEVICE, AND COMPUTED TOMOGRAPHY DEVICE

PRIORITY STATEMENT

The present application hereby claims priority under 35 U.S.C. § 119 to German patent application number DE 102018204517.8 filed Mar. 23, 2018, the entire contents of which are hereby incorporated herein by reference.

FIELD

Embodiments of the invention generally relate to a method for generating images via a computed tomography device, in particular via a computed tomography device which uses two different X-ray spectra for X-raying an object; and to a computed tomography device.

BACKGROUND

In X-ray imaging, particularly in the medical field, methods are frequently used in which the object to be observed, in particular the body of a patient, is irradiated with two different X-ray spectra in order to be able to better represent different tissue types, for example. The X-ray images generated with these different X-ray spectra are usually combined with one another for the representation. An X-ray imaging technique also referred to as "split-filter" or "twin-beam dual-energy" computed tomography is optionally used here. In this case, a beam filter is introduced into the beam path between the X-ray source and the X-ray detector, which beam filter splits the X-ray beam into two beam ranges (or: partial beams), which are respectively assigned to one of the two X-ray spectra.

The X-ray detector is in this case illuminated area-by-area with the different X-ray spectra. These areas of the X-ray detector are usually arranged adjacent to one another, viewed in the direction of travel of a patient table (also referred to as a patient couch). Choosing a suitable pitch (a ratio of the table travel per revolution of the X-ray source and the slice thickness to be examined) ensures that the same slice of the object (i.e. of the patient) is scanned with both spectra during a spiral scan, there being a time offset of usually one gantry rotation between the two images generated with the different X-ray spectra. As a result of the time offset, the examination objects within the respective slice (for example, the heart, blood vessels and other organs) recorded via the respective detector area may have moved significantly.

Due to such movements, differences can occur between the images captured with the two detector areas, which differences can lead to image artifacts when the two images are analyzed together with so-called dual-energy algorithms (for example, a so-called base material decomposition). While it is known in the field of X-ray imaging for images captured under different conditions to be registered to one another, i.e. in particular for the structures of one image to be deformed such that they match the corresponding structures of the other image and consequently overlay these, these methods, too, can reach their limits, in particular if movements within the areas of the image differ sharply locally.

From printed publication DE 0 2009 007 236 A1 a method for scanning a moving examination object with a CT system is known, in which data is recorded during a rotating movement of a transmitter/receiver pair about the examination object. Furthermore, sectional images of the examination object are determined from the data via an iterative algorithm, motion information relating to motion of the examination object during the data recording being included in the iterative algorithm.

From printed publication DE 10 2011 007 529 A1 a method, a radiation therapy system and a combination of CT system and radiation therapy system for determining a motion profile of a moving object in an examination object with an emitter-detector system displaceable relative to the examination object are known, the following method steps being executed:

scanning of the examination object in the region of the moving object during a displacement of the emitter-detector system relative to the examination object and generation of a pixel data set with attenuation values over time, removal of fixed structures from the pixel data set, determination of an attenuation value induced by the moving object in each detector row at a plurality of successive time points of the scan and formation of a 3D data set from the values of the attenuation maximum of the detector rows over the detector rows and the readout times of the scan, and determination of at least one of the values from the following list from the result data set: frequency and/or phase and/or amplitude of the motion of the object, area of location of the object during the scan, position of the object at a predefined phase of the motion.

From printed publication DE 10 2011 083 647 A1 a method for generating a motion-compensated CT image data set is known, wherein:

a projection data set of a CT system is recorded from a predefined motion phase and a projection angle range, which projection data set allows the reconstruction of a CT image data set, the motion field is determined iteratively by:

multiple reconstruction of the one CT image data set with a first image resolution with a motion-compensating reconstruction method using a first analytical reconstruction algorithm and different motion fields from each of a plurality of location-specific motion vectors, and determination of the motion field using at least one predefined constraint, and reconstruction of a final CT image data set with a second image resolution using a motion-compensating reconstruction method based on a second reconstruction algorithm and the determined motion field.

SUMMARY

At least one embodiment of the invention enables improved X-ray imaging.

At least one embodiment of the invention is directed to a method. Furthermore, at least one embodiment of the invention is directed to a computed tomography device. Advantageous and in part per se inventive embodiments and developments of the invention are described in the claims and the description below.

At least one embodiment of the invention is directed to a method for generating images via a computed tomography device, in which a first row area of a multiple-row detector is illuminated with a first X-ray spectrum and a second row area of the multiple-row detector, trailing in a direction of travel, is illuminated with a second X-ray spectrum, the method comprising:

recording image data at a pitch chosen such that one slice image is reconstructable for a sectional position for each of the first row area and the second row area;

reconstructing, for the sectional position for each of the first row area and the second row area, a respective slice image for the first row area and a respective slice image for the second row area;

reconstructing a reference sectional image for a third row area, illuminated with the first X-ray spectrum and the second X-ray spectrum, as a slice image; and registering to the reference sectional image, to generate motion-reduced respective first spectral images and second spectral images, respectively assigned to the first row area and the second row area, the respective slice images of the first row area and second row area.

At least one embodiment of the invention is directed to a computed tomography device, comprising:

an X-ray source;

a multiple-row detector, in which a first row area of the multiple-row detector is illuminatable with a first X-ray spectrum and a second row area of the multiple-row detector, trailing in a direction of travel, is illuminatable with a second X-ray spectrum; and a control and analysis computer, configured to implement at least recording image data at a pitch chosen such that one slice image is reconstructable for a sectional position for each of the first row area and the second row area;

reconstructing, for the sectional position for each of the first row area and the second row area, a respective slice image for the first row area and a respective slice image for the second row area;

reconstructing a reference sectional image for a third row area, illuminated with the first X-ray spectrum and the second X-ray spectrum, as a slice image; and registering to the reference sectional image, to generate motion-reduced respective first spectral images and second spectral images, respectively assigned to the first row area and the second row area, the respective slice images of the first row area and second row area.

A method for generating images via a computed tomography device, configured to generate first and second X-ray spectra which differ from one another, the method comprising:

recording image data at a pitch chosen such that at least two slice images are reconstructable for a sectional position for each of the first X-ray spectrum and the second X-ray spectrum;

reconstructing, for the sectional position for each of the first X-ray spectrum and the second X-ray spectrum, a respective at least two slice images for the first X-ray spectrum and a respective at least two slice images for the second X-ray spectrum; and gradually registering, to generate a motion-reduced first spectral image assigned to the first X-ray spectrum and second spectral image assigned to the second X-ray spectrum, the respectively assigned at least two slice images for the first X-ray spectrum and the at least two slice images for the second X-ray spectrum, to one another.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

BRIEF DESCRIPTION OF THE DRAWINGS

Example embodiments of the invention will be described in greater detail below with reference to a drawing, in which.

Corresponding parts and variables are always labeled with the same reference characters in all the figures.

DETAILED DESCRIPTION OF EXAMPLE EMBODIMENTS

Figure 1:
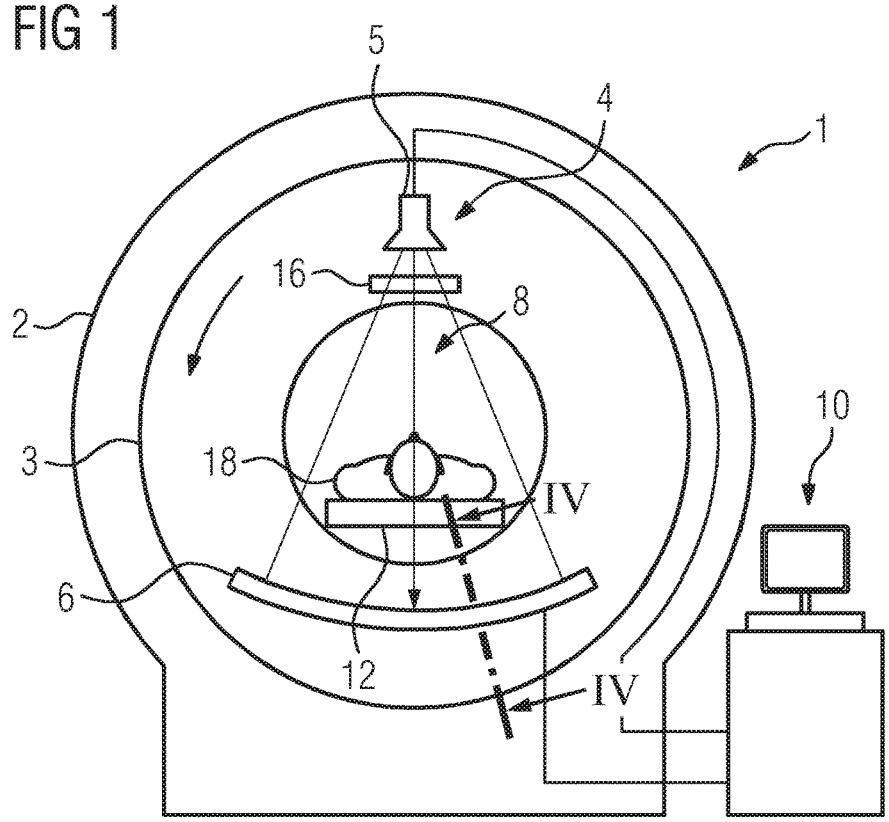
FIG. 1 shows a computed tomography device in a schematic front view.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the" are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

A purpose of the method according to an embodiment of the invention is to generate images via a computed tomography device. In this computed tomography device (in particular, when operated for the purpose intended) a first row area of a multiple-row detector is illuminated (preferably only) with a first X-ray spectrum and a second row area of the multiple-row detector, the second row area trailing in the direction of travel (which is preferably perpendicular to the direction of the rows of the detector), is illuminated (preferably only) with a second X-ray spectrum. According to the method, image data is captured here at a pitch chosen such that for a sectional position one slice image for the first and the second row area can be reconstructed in each case.

Correspondingly, the respective slice image for the first and the second row area is also reconstructed for the sectional position. For a third row area, which is arranged in particular between the first and the second row area, and which (during operation for the purpose intended) is illuminated with the first and the second X-ray spectrum, a reference sectional image is reconstructed as a slice image. To generate motion-reduced first and second spectral images assigned to the respective first and second row area, the slice images of the respective first and second row areas are then registered to the reference sectional image of the third row area.

The term "sectional position" is understood here and below to mean, in particular, a position of a sectional plane through the object to be examined, in particular through the patient, for which a (slice) image is to be calculated. At least one subarea of the raw data recorded during the CT spiral scan is used to calculate this image. For the calculation of an image, particularly in order to be able to capture the fullest possible information about the object at the respective sectional position, multiple partial revolutions of an X-ray system composed of an X-ray source and the associated detector are usually required, in particular in order also to able to map the subarea of the patient located at the sectional position to a sufficient number of detector rows in each case.

The term "register" is understood here and below to mean, in particular, that the contours and/or structures of an image are deformed such that they can be brought into alignment with the corresponding contours and/or structures of another (target) image. So-called "non-rigid" registration algorithms are preferably used for registration. The term "row area" is understood here and below to mean, in particular, a number of detector rows (arranged in particular adjacent to one another) which are each illuminated by one or both X-ray spectra.

As the illumination of the first and second row areas at the relevant sectional position occurs, due inter alia to the pitch and the desired view of one and the same object structure, at a different time (separated by the time of at least one partial revolution of the X-ray system, in particular of at least one complete revolution), the object structure to be observed may possibly have moved significantly. This is because motion periods of organs, for example of the heart or blood vessels or similar, are frequently of the order of fractions of a second. As a result, the displacements between the (image) structures recorded with the respective X-ray spectra may be so large that conventional registration methods are no longer applicable or lead to an unsatisfactory result.

An embodiment of the invention proceeds from the recognition that the third row area illuminated with both X-ray spectra, which is unsuitable for the image analysis of in particular "spectrally pure" radioscopic images, contains geometric information which, due to its irradiation with both X-ray spectra, is in particular time-averaged. The image information contained in this third row area, which is not usually used for analysis, is now advantageously used in order to reduce, in particular to approximately halve, a "step width" in the registration of the two spectrally pure slice images of the first and the second row area. In other words, the geometric information contained in the third row area is used in order to bring the structures which moved between the capture of the slice image of the first row area and the capture of the slice image of the second row area closer to one another. In this way, motion artifacts in the representation or further analysis of the slice images (in particular of the motion-reduced spectral images resulting therefrom) of the first and second row area can advantageously be reduced and the quality of image generation consequently improved.

In a preferred embodiment of the method, the slice images of the first and second row areas, which have been registered to the reference sectional image are (also) registered to one another to generate the first and second spectral images. For example, the slice image of the first row area is registered to the slice image of the second row area (or vice versa). This advantageously further reduces, in particular completely removes or reduces to an at least negligible level, the residual motion differences.

In a further preferred embodiment of the method, a value of less than or equal to 0.5 is used for the pitch.

In a useful embodiment of the method, the first and the second row area are illuminated with the respective first and second X-ray spectrum, a beam filter for the spectral subdivision of the X-ray beam being introduced (in particular viewed in the direction of travel) into the beam path of an X-ray beam of the computed tomography device between the X-ray source and the multiple-row detector. It is advantageously possible in this case to keep the design outlay on the computed tomography device for generating images with different X-ray spectra low. In particular, it is also possible, preferably by using a beam filter which can be reversibly moved into the beam path, to use the same computed tomography device also for conventional—i.e. operating in particular with an X-ray beam which is not spectrally subdivided—image generation methods.

In a further useful embodiment of the method, which also constitutes an embodiment of an independent invention and which as an embodiment of an independent invention is basically independent of the spectral subdivision of the detector rows of an individual detector into the above-described two or three row areas, by illuminating with the different first and second X-ray spectra, for the first and the second X-ray spectrum respectively at least two (in particular independent of one another) slice images, which in particular each represent a different recording time, are respectively reconstructed for the corresponding sectional position. To generate the motion-reduced first and second spectral images assigned to the first and second X-ray spectrum respectively. the respective slice images assigned to the first and second X-ray spectrum are gradually (and in particular successively) registered to one another. I.e. preferably taking into account their temporally staggered generation at the respective sectional position, the individual slice images are registered successively to the temporally adjacent slice image. The gradual registration also enables inter alia motion reduction as early as during reconstruction.

Detector rows that differ from one another are preferably used for the (in particular independent) reconstruction of the respective at least two slice images of an X-ray spectrum.

Independently of the illumination described in the introduction of a single detector with the two different X-ray spectra, an embodiment of an independent invention described above is, however, also advantageous for computed tomography devices which have two separate X-ray systems—i.e. two different X-ray sources and two separate detectors—for generating the different X-ray spectra and consequently the different spectral images. These two separate X-ray systems are usually arranged offset by 90 degrees relative to one another on the gantry of the computed tomography device so that here too a temporal offset exists between the respective spectral images and the slice images possibly forming these. In this case, image data is consequently also captured at a pitch chosen such that for the corresponding sectional position in each case at least two slice images, which in particular each represent a different time of capture, can be reconstructed for the first and the second X-ray spectrum. Based on this image data, the at least two slice images are also each reconstructed for the sectional position for the first and the second X-ray spectrum. These slice images are then gradually (and in particular consecutively in their temporal sequence) registered to one another to generate the respective motion-reduced first and second spectral images assigned to the first X-ray spectrum and second X-ray spectrum respectively.

In a preferred development of the method embodiment described above—in which for each X-ray spectrum, in particular for each first and second row area of the single multiple-row detector, multiple slice images are reconstructed—the respective slice images assigned to the first X-ray spectrum are registered to one another, in particular in ascending order, to generate the motion-reduced first spectral image assigned to the first X-ray spectrum. To generate the motion-reduced second spectral image assigned to the second X-ray spectrum, the respective slice images assigned to the second X-ray spectrum are correspondingly registered to one another, in particular in descending order.

The terms "ascending" and "descending" are used here and below to refer in particular to the direction of travel and/or the temporal sequence. Consequently, "ascending" means in particular that the temporally first sectional image and consequently the sectional image which is preceding in the direction of travel is registered to the slice image which is temporally trailing at the same sectional position. "Descending" correspondingly means conversely that the temporally last slice image—which viewed in the direction of travel is consequently recorded with a trailing area of the detector—is registered to the respectively temporally preceding slice image. Particularly where the two X-ray spectra are recorded with the above-described first and second row areas respectively of the (in particular only one) multiple-row detector, the result is consequently advantageously that the slice images forming the respective spectral image are, in particular viewed temporally, brought closer to one another from opposing directions.

Viewed geometrically in relation to the detector, in particular the slice images assigned to the outer detector areas (viewed transversely relative to the row direction of the detector) are registered, gradually toward the center of the detector, to the respective slice images lying further inward. Consequently, the motion offset within the respective X-ray spectrum (and in particular of the respective first and second row area) is gradually aligned in the direction of the "temporal center" between the recording of the two X-ray spectra in particular by way of the two row areas.

In a further useful method embodiment, the respective slice images registered to one another which are assigned to the respective X-ray spectrum are in particular gradually combined with one another. In particular, the image information contained in the respective slice images is integrated in a resulting joint slice image, hereinafter also referred to as the "composite slice image". For example, the slice images registered to one another are averaged for this purpose or are preferably added together linearly weighted in a noise-optimizing manner. Particularly where more than two slice images are reconstructed for the respective X-ray spectrum, the composite slice image formed by combining the two preceding slice images is preferably registered to the subsequent slice image and preferably combined with the latter in turn. Advantageously as a result the spectral image resulting from the individual sectional images contains all the information of the individual slice images. Alternatively, all the slice images of an X-ray spectrum are first, as described above, registered to one another and only then combined with one another.

In a preferred method embodiment, particularly where at least two slice images are reconstructed for each X-ray spectrum, a value of about 0.3 is used for the pitch.

To generate the motion-reduced first and second spectral images, the at least two slice images which have been registered to one another, of one of the two X-ray spectra are preferably also registered to the corresponding slice images (registered to one another) (for example the composite slice images) of the other X-ray spectrum. In particular, the above-described partial composite images formed from in particular all the slice images recorded for the respective X-ray spectrum are registered to one another. This method embodiment is in particular independent of the above-described registration to the reference sectional image which is reconstructed from the image data of the above-described third row area.

In an optional method embodiment, in a computed tomography device with two separate X-ray systems the slice images assigned to the respective X-ray spectrum are registered within the respective detector from both sides to the "temporal center", which in particular corresponds to the geometric center of the detector, and in particular then also registered to one another.

In a further useful method embodiment, which is implemented in particular during illumination of the single detector with the two X-ray spectra, in particular multiple partial revolutions of the (in particular single) X-ray system (also called the "projection system") are used for the relevant sectional position so that within the multiple-row detector at least five slice images can be reconstructed at the same sectional position. In the case of the reconstruction of precisely five slice images, in particular two slice images respectively are assigned to the first and the second row area and one slice image is assigned to the third row area.

Preferably, however, so many partial revolutions are used that three or more slice images can be reconstructed for the first and the second row area. The individual slice images thereby advantageously have mainly comparatively small motion-caused displacements and consequently deviations from one another which can be reduced particularly easily by the above-described gradual registration in ascending and descending order. In this case, the slice images reconstructed for the first and second row area and gradually registered to one another—and optionally combined with one another—are particularly preferably first registered to the reference sectional image of the third row area and then to one another. This advantageously combines the advantages which through the use of the "spectrally contaminated" third row area with regard to the temporally averaged geometric information contained therein and the gradual registration (also forming an independent invention) of multiple independent slice images within the respective first and second row areas.

In a further useful method embodiment, the first and second spectral images which have been motion-reduced in the manner described above are analyzed via an analysis algorithm for the image analysis of "multi-energy X-ray images" (for example, a so-called base material decomposition).

In yet another useful method embodiment, the spectral images which have been motion-reduced in the manner described above are used to generate motion-reduced X-ray images from the image data by way of a fresh reconstruction.

The method described above is advantageously also used if more than two X-ray spectra are used in particular for illuminating the (preferably one multiple-row) detector (for example using a triply or multiply effective beam filter).

The computed tomography device according to an embodiment of the invention also comprises in addition to the at least one X-ray system a control and analysis computer (also called a "reconstruction computer") which is configured to implement the above-described method automatically or possibly in interaction with a user.

In a preferred embodiment, the reconstruction computer is composed at least in essence of a microcontroller with a processor and a data memory, in which the functionality for performing the method according to an embodiment of the invention is implemented from a programming perspective in the form of operating software (firmware) such that the method—possibly in interaction with a device user, for example a radiologist—is performed automatically when the operating software is executed in the microcontroller.

In a useful embodiment, the above-described computed tomography device comprises the beam filter positioned or in particular reversibly positionable between the X-ray source and the detector, which beam filter, when the computed tomography device is operated for the purpose intended within the framework of the method described above, serves to spectrally subdivide the X-ray beam into at least the first and the second X-ray spectrum.

Figure 2:
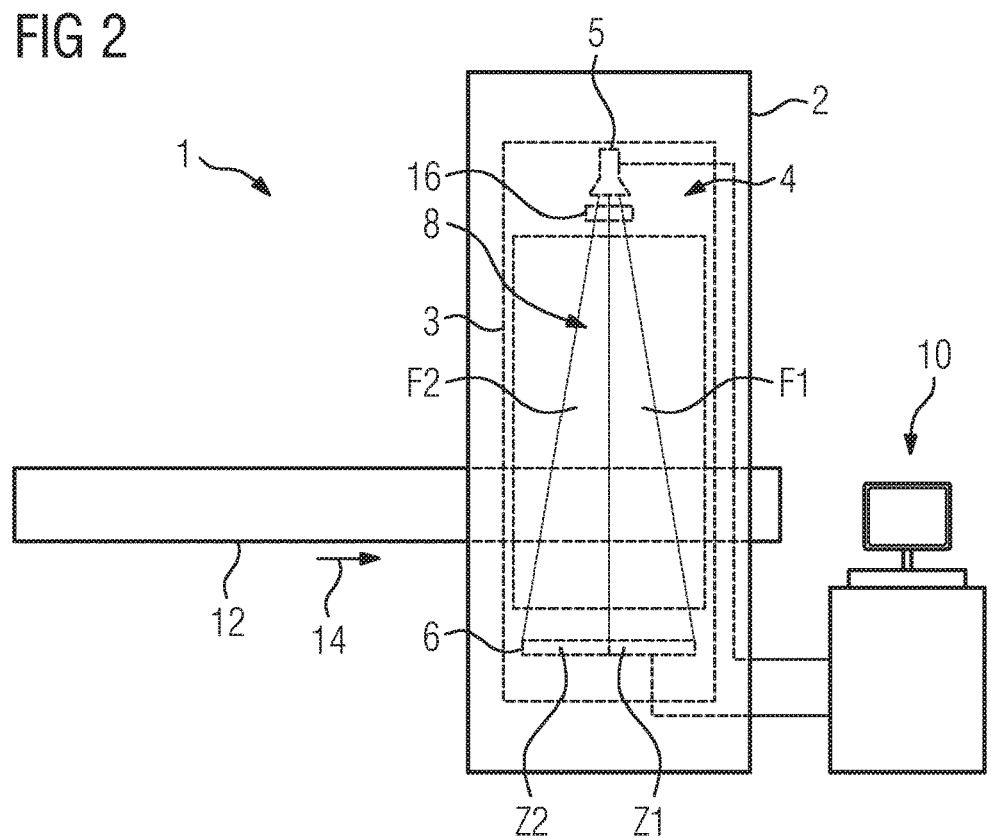
FIG. 2 shows the computed tomography device in a side view.

FIGS. 1 and 2 show schematically a computed tomography device 1. The computed tomography device 1 comprises a holding frame 2, which holds an annular turntable (also referred to as a "gantry 3"). The gantry 3 is rotatably mounted relative to the holding frame 2. The gantry 3 in turn holds an X-ray system 4, which is composed of an X-ray source 5 and an (X-ray) detector 6 arranged opposite the former. The X-ray source 5 serves to emit an X-ray beam 8 in the form of a fan beam in the direction of the detector 6. To control and regulate the X-ray source 5 and to record and analyze the raw image data recorded via the detector 6—which data reflects an intensity curve of the incident X-ray radiation—the X-ray source 5 and the detector 6 are connected for signal transmission to a control and analysis computer, hereinafter referred to in short as a "reconstruction computer 10". The computed tomography device 1 further comprises a patient couch 12, which when operated for the purpose intended is arranged in an interior space of the gantry 3 and is movable along a direction of travel 14.

In order with the only one detector 6 to enable a display of X-ray images generated with in each case different X-ray spectra and thus with different X-ray energies, the computed tomography device 1 comprises a beam filter 16 which when operated for the purpose intended is arranged in the beam path between the X-ray source 5 and the detector 6, specifically between the X-ray source 5 and a measurement object (i.e. a patient 18). The beam filter 16 is embodied such that the X-ray beam 8 viewed in the direction of travel 14 is subdivided into two partial beams, namely a first partial beam with a first X-ray spectrum F1 and a second partial beam with a second X-ray spectrum F2 which is different from the first X-ray spectrum F1 (cf. FIG. 2). Due to this spectral subdivision of the X-ray beam 8, a first row area Z1 of the detector 6 viewed in the direction of travel 14 is illuminated with the first X-ray spectrum F1 and a second row area Z2 trailing in the direction of travel 14 is illuminated with the second X-ray spectrum F2. To generate images via this X-ray system 4, a method which will be described in greater detail below is implemented by the reconstruction computer 10.

Figure 3:
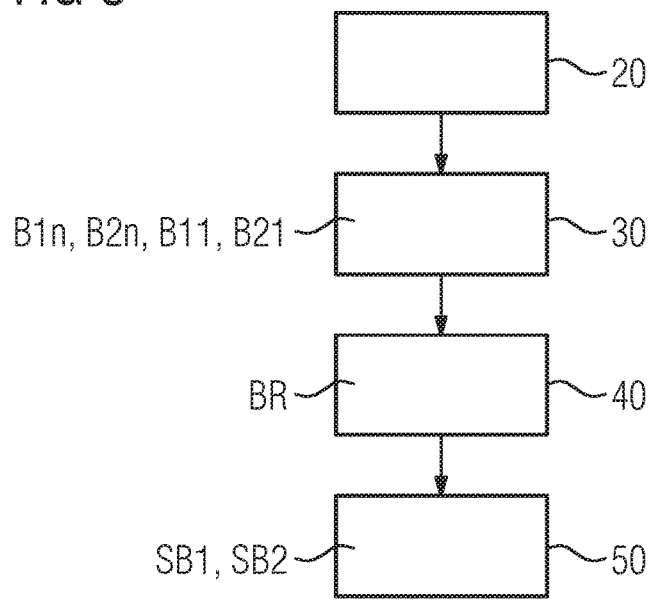
FIG. 3 shows in a schematic flow diagram a method for generating images via the computed tomography device.
Figure 4:
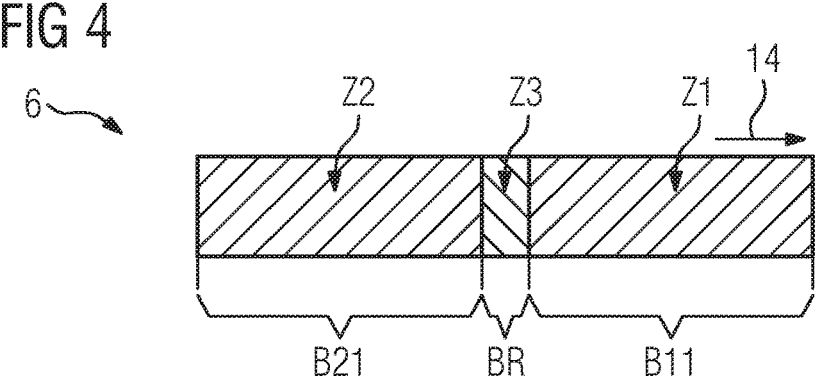
FIG. 4 shows in a schematic sectional view IV-IV in accordance with FIG. 1 a detector of the computed tomography device implementing an embodiment of the image generation method.

FIG. 3 shows the (image generation) method implemented by the reconstruction computer 10 schematically with the aid of a flow diagram. In a first method step 20, image data is captured, the gantry 3 rotating while the X-ray beam 8 is emitted and the patient couch 12 being displaced in the direction of travel 14. This results in a spiral scan of the examination area of the patient 18. In this process, a so-called pitch is chosen such that a slice image B1n and B2n respectively can be reconstructed for a sectional position for the first and the second row area Z1 and Z2 of the detector 6. The index n here represents an integer counter and can consequently assume values 1, 2, 3 etc. In this case, therefore, the entire first and second row area Z1 and Z2 respectively is used to reconstruct the corresponding first and second slice image B11 and B21 (cf. FIG. 4). The reconstruction of the first and second slice image B11 and B21 for the respective row area Z1 and Z2 at the corresponding sectional position takes place in a second method step 30.

In a further method step 40, a reference sectional image BR is reconstructed for a third row area Z3, which, viewed in the direction of travel 14, is arranged between the first and the second row area Z1 and Z2 and which during operation of the X-ray system 4 is always illuminated with X-ray radiation of both X-ray spectra F1 and F2.

In a subsequent method step 50, to generate motion-reduced first and second spectral images SB1 and SB2 the slice images B11 and B21 are each first registered to the reference sectional image BR. Due to the spatial distance between the first and the second row area Z1 and Z2, the X-raying of the patient 18 with the second row area Z2 takes place at the same sectional position at a later time than with the first row area Z1. In this way, structures to be examined, such as e.g. organs, may have moved due to their inherent independent motions (for example heartbeat or similar), so that the structures of the slice images B11 and B21 no longer overlap when the two images are "simply laid on top of one another". The image data recorded by way of the third row area Z3 does not enable a spectrally pure representation and is consequently not usable for medical analysis, but it does contain geometric information that has been averaged at least from a temporal viewpoint. This information is used by the registration of the two slice images B11 and B21 to the reference sectional image BR generated from the third row area Z3 to reduce the motion difference between the two "spectrally pure" slice images B11 and B21. Following registration to the reference sectional image BR, the two slice images B11 and B21 are also registered to one another so that the residual motion differences can be reduced with a high degree of precision.

In a further example embodiment (shown with the aid of FIG. 5) the pitch is chosen such that for each row area Z1 and Z2 multiple slice images B11 to B14 and B21 to B24 respectively can be generated. For example, the pitch here is 0.3. In method step 30, the multiple slice images B1n and B2n are correspondingly also reconstructed, different detector rows being used in each case for each slice image B1n and B2n. In method step 50, the slice images B1n viewed in the direction of travel 14 are registered to one another in ascending order and the slice images B2n are registered to one another in descending order.

Figure 5:
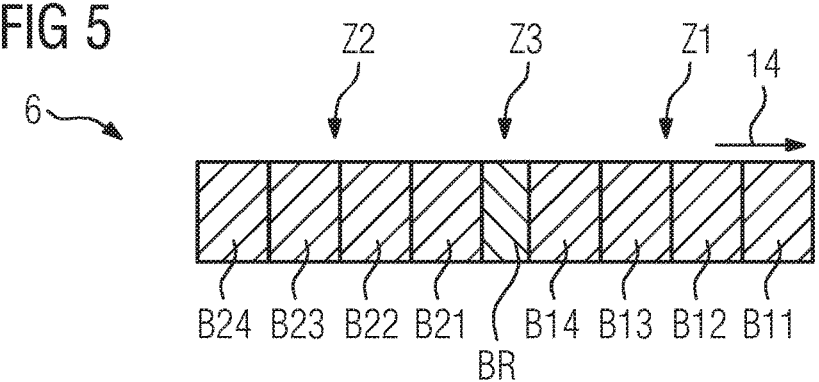
FIG. 5 shows the detector implementing an alternative method embodiment.

In the sectional view of the detector six shown in FIG. 5, the respective slice images B11 to B14 and B21 to B24 are in each case registered to one another transversely relative to the row direction of the detector 6 from the outer sides of the detector 6 towards the center. Specifically, for the first row area Z1 the slice images B11, B12, B13 and B14 are registered to one another in ascending order and correspondingly for the second row area Z2 the slice images B24, B23 to B21 are registered to one another in descending order.

After the respective registration of an outside slice image B1n or B2n to the next slice image toward the inside B1n or B2n, the two respective slice images (for example B11 and B12 or B24 and B23) are combined with one another such that their respective information is combined in a shared composite slice image. After all the spectrally pure slice images B1n and B2n toward the center of the detector have been registered to one another, the resulting composite slice image for generating the respective motion-reduced spectral image SB1 and SB2 is first registered to the reference sectional image BR. Then the spectral image SB1 assigned to the first row area Z1 is registered to the second spectral image SB2. Alternatively, this "final" registration can also be carried out in reverse order.

Figure 6:
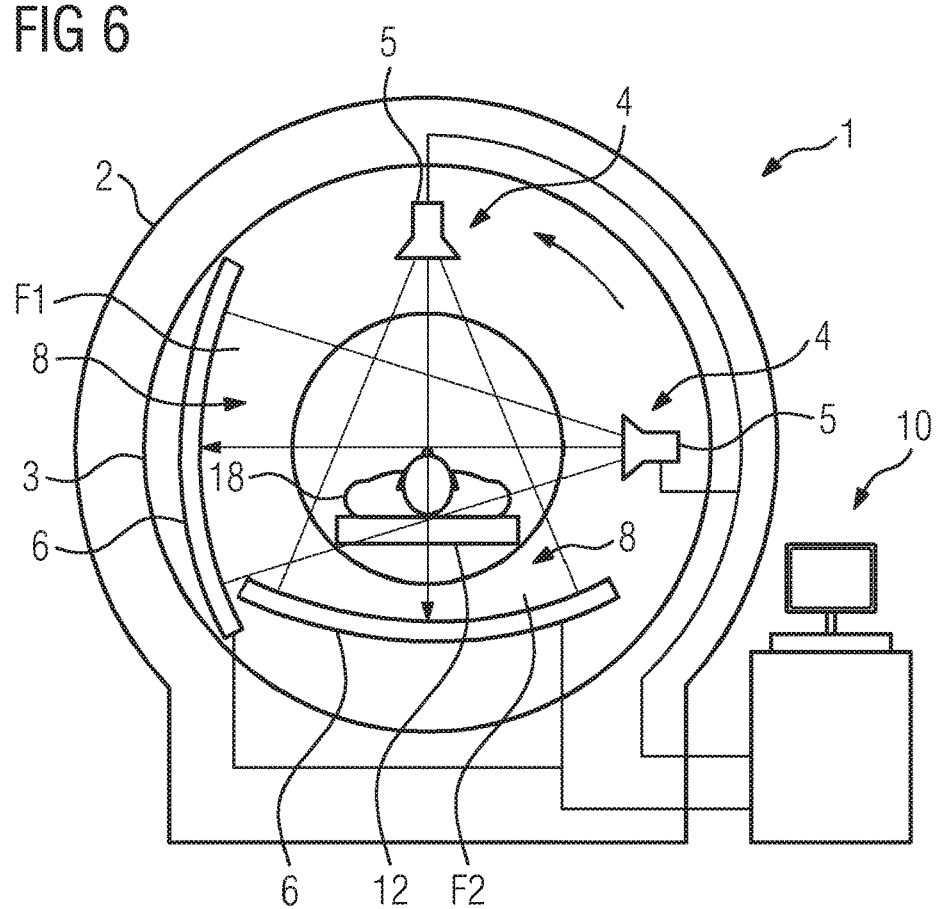
FIG. 6 shows in a view in accordance with FIG. 1 an alternative computed tomography device.

FIG. 6 shows an alternative example embodiment of the computed tomography device 1. In this example embodiment, the gantry 3 holds two X-ray systems 4, which are arranged offset by 90 degrees to one another on the gantry 3. One of the two X-ray systems 4 is operated with the first X-ray spectrum F1 and the other X-ray system 4 is operated with the second X-ray spectrum F2. Consequently, when the computed tomography device 1 is operated for the purpose intended, one complete detector 6 respectively is illuminated with one X-ray spectrum F1 or F2 respectively. Due to the angular offset between the two X-ray systems 4, at least individual detector rows of the two detectors 6 are illuminated at the respective sectional position at different times. The image generation method implemented by the reconstruction computer 10 partially corresponds in this example embodiment to the method described hereinabove.

Figure 7:
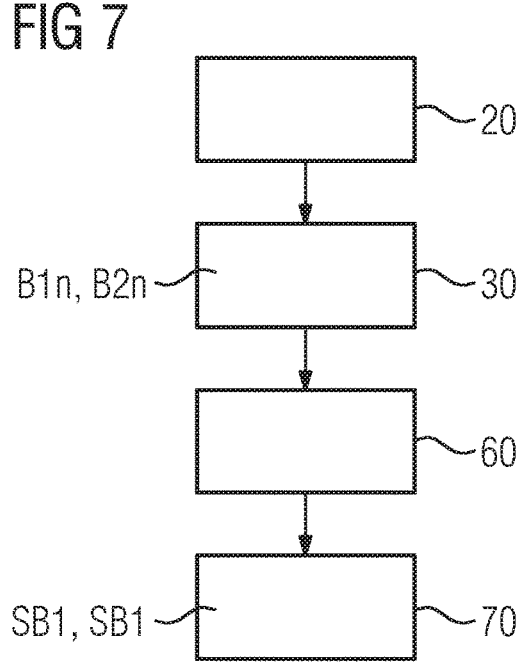
FIG. 7 shows in a view in accordance with FIG. 3 an alternative image generation method which is implemented via the computed tomography device in accordance with FIG. 6.

As shown in FIG. 7, in the method step 20 image data is first captured analogously to the method described hereinabove. In the method step 30, for each of the two detectors 6—and not only for a row area narrower that the detector width—and consequently for the respective X-ray spectrum F1 and F2 the slice images B1n and B2n are reconstructed.

In a further method step 60, the respective slice images B1n and B2n are then (again within one of the two detectors 6) gradually registered to one another (compare the method step 50 as shown in FIG. 3). Specifically, however, the slice images B1n and B2n of the respective X-ray spectrum F1 and F2 are registered to one another from both sides of the respective detector 6 toward the center thereof. In the event that for each detector 6 five slice images B11 to B15 and b21 to B25 are reconstructed respectively, consequently the slice images B11 and B12 are registered in ascending order to the slice image B13 and the slice images B15 and B14 are registered in descending order to the slice image B13 (the same applies to the slice images B21 to B25). A temporally averaged spectral image SB1 and SB2 is thereby created in each case for the respective detector 6. The two spectral images SB1 and SB2 are then registered to one another to reduce residual motion differences.

The subject matter of the invention is not restricted to the example embodiments described hereinabove. Rather, further embodiments of the invention may be derived from the description hereinabove by a person skilled in the art. In particular, the individual features of the invention and design variants thereof described with the aid of the various example embodiments may be combined with one another in another manner.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating images via a computed tomography device, in which a first row area of a multiple-row detector is illuminated with a first X-ray spectrum and a second row area of the multiple-row detector, trailing in a direction of travel, is illuminated with a second X-ray spectrum, the method comprising:
   recording image data at a pitch chosen such that one slice image is reconstructable for a sectional position for each of the first row area and the second row area;
   reconstructing, for the sectional position for each of the first row area and the second row area, a respective slice image for the first row area and a respective slice image for the second row area;
   reconstructing a reference sectional image for a third row area, illuminated with the first X-ray spectrum and the second X-ray spectrum, as a slice image; and
   registering to the reference sectional image, to generate motion-reduced respective first spectral images and second spectral images, respectively assigned to the first row area and the second row area, the respective slice images of the first row area and second row area.

2. The method of claim 1, wherein to generate the motion-reduced respective first spectral images and second spectral images, the slice images of the first row area and the slice images of the second row areas, registered to the reference sectional image, are registered to one another.

3. The method of claim 2, wherein a value less than or equal to 0.5 is used for the pitch.

4. The method of claim 2, wherein the first row area and the second row area are illuminated with the first X-ray spectrum and the second X-ray spectrum, respectively, a beam filter for spectral subdivision of the X-ray beam being introduced into a beam path of an X-ray beam of the computed tomography device between an X-ray source and the multiple-row detector.

5. The method of claim 2, wherein for the sectional position, multiple partial revolutions of an X-ray system composed of an X-ray source and the multiple-row detector are used so that inside the multiple-row detector, at least five slice images are reconstructable.

6. The method of claim 2, wherein the first spectral images and the second spectral images are analyzed via an analysis algorithm for analysis of multi-energy X-ray images.

7. The method of claim 1, wherein a value less than or equal to 0.5 is used for the pitch.

8. The method of claim 7, wherein the first row area and the second row area are illuminated with the first X-ray spectrum and the second X-ray spectrum, respectively, a beam filter for spectral subdivision of the X-ray beam being introduced into a beam path of an X-ray beam of the computed tomography device between an X-ray source and the multiple-row detector.

9. The method of claim 1, wherein the first row area and the second row area are illuminated with the first X-ray spectrum and the second X-ray spectrum, respectively, a beam filter for spectral subdivision of an X-ray beam being introduced into a beam path of an X-ray beam of the computed tomography device between an X-ray source and the multiple-row detector.

10. The method of claim 1, wherein for the sectional position, multiple partial revolutions of an X-ray system composed of an X-ray source and the multiple-row detector are used so that inside the multiple-row detector, at least five slice images are reconstructable.

11. The method of claim 1, wherein the first spectral images and the second spectral images are analyzed via an analysis algorithm for analysis of multi-energy X-ray images.

12. The method of claim 1, wherein, based on the motion-reduced spectral images, a reconstruction of images from the recording image data is carried out afresh.

13. A method for generating images via a computed tomography device, configured to generate a first X-ray spectrum and a second X-ray spectrum which differ from one another, the method comprising:
   recording image data at a pitch chosen such that at least two slice images are reconstructable for a sectional position for each of the first X-ray spectrum and the second X-ray spectrum;
   reconstructing, for the sectional position for each of the first X-ray spectrum and the second X-ray spectrum, a respective at least two slice images for the first X-ray spectrum and a respective at least two slice images for the second X-ray spectrum; and
   gradually registering, to generate a motion-reduced first spectral image assigned to the first X-ray spectrum and a motion-reduced second spectral image assigned to the second X-ray spectrum, respectively assigned at least two slice images for the first X-ray spectrum and the at least two slice images for the second X-ray spectrum, to one another.

14. The method of claim 13, wherein
   to generate the first spectral image assigned to the first X-ray spectrum, the at least two slice images assigned to the first X-ray spectrum are registered to one another in ascending order, and
   to generate the second spectral image assigned to the second X-ray spectrum, the at least two slice images assigned to the second X-ray spectrum are registered to one another in descending order.

15. The method of claim 14, wherein at least one of
   the respective at least slice images of the first X-ray spectrum registered to one another are combined with one another, and
   the respective at least slice images of the second X-ray spectrum registered to one another are combined with one another.

16. The method of claim 14, wherein to generate the motion-reduced first spectral image and the motion-reduced second spectral image, the slice images of each of the first X-ray spectrum and the second X-ray spectrum, registered to one another, are registered to one another.

17. The method of claim 13, wherein at least one of
   the respective at least slice images of the first X-ray spectrum registered to one another are combined with one another, and the respective at least slice images of the second X-ray spectrum registered to one another are combined with one another.

18. The method of claim 13, wherein to generate the motion-reduced first spectral image and the motion-reduced second spectral image, the slice images of each of the first X-ray spectrum and the second X-ray spectrum, registered to one another, are registered to one another.

19. A computed tomography device, comprising:
an X-ray source;
a multiple-row detector, in which a first row area of the multiple-row detector is illuminatable with a first X-ray spectrum and a second row area of the multiple-row detector, trailing in a direction of travel, is illuminatable with a second X-ray spectrum; and
a control and analysis computer, configured to implement at least
recording image data at a pitch chosen such that one slice image is reconstructable for a sectional position for each of the first row area and the second row area;
reconstructing, for the sectional position for each of the first row area and the second row area, a respective slice image for the first row area and a respective slice image for the second row area;
reconstructing a reference sectional image for a third row area, illuminated with the first X-ray spectrum and the second X-ray spectrum, as a slice image; and
registering to the reference sectional image, to generate motion-reduced respective first spectral images and second spectral images, respectively assigned to the first row area and the second row area, the respective slice images of the first row area and second row area.

20. The computed tomography device of claim 19, further comprising:
a beam filter for spectral subdivision of an X-ray beam, the beam filter being positioned or positionable between the X-ray source and the multiple-row detector.

* * * * *